United States Patent
Yount et al.

(10) Patent No.: US 10,006,698 B2
(45) Date of Patent: Jun. 26, 2018

(54) USING METHANE REJECTION TO PROCESS A NATURAL GAS STREAM

(71) Applicant: GE Oil & Gas, Inc., Houston, TX (US)

(72) Inventors: Christopher Scott Yount, San Antono, TX (US); John Raymond Zigtema, San Antonio, TX (US)

(73) Assignee: GE Oil & Gas, Inc., Houston, TX (US)

( * ) Notice: Subject to any disclaimer, the term of this patent is extended or adjusted under 35 U.S.C. 154(b) by 214 days.

(21) Appl. No.: 14/809,997

(22) Filed: Jul. 27, 2015

(65) Prior Publication Data

US 2017/0030634 A1 Feb. 2, 2017

(51) Int. Cl.
*F25J 3/02* (2006.01)
*C01B 31/20* (2006.01)
*C07C 7/00* (2006.01)
*C10L 3/10* (2006.01)

(52) U.S. Cl.
CPC ............. *F25J 3/0233* (2013.01); *C01B 31/20* (2013.01); *C07C 7/00* (2013.01); *C10L 3/104* (2013.01); *F25J 3/0209* (2013.01); *F25J 3/0266* (2013.01); *C01B 2210/0009* (2013.01); *C10L 2290/10* (2013.01); *C10L 2290/46* (2013.01); *C10L 2290/543* (2013.01); *F25J 2200/04* (2013.01); *F25J 2200/70* (2013.01); *F25J 2215/04* (2013.01); *F25J 2230/08* (2013.01); *F25J 2245/02* (2013.01); *F25J 2260/20* (2013.01); *Y02C 10/12* (2013.01); *Y02P 20/152* (2015.11)

(58) Field of Classification Search
CPC ........ F25J 3/067; F25J 3/0266; F25J 2220/80; F25J 2220/82
See application file for complete search history.

(56) References Cited

U.S. PATENT DOCUMENTS

| 2,888,807 | A | * | 6/1959 | Bocquet | C07C 7/04 62/630 |
| 4,462,814 | A | | 7/1984 | Holmes et al. | |
| 5,139,544 | A | | 8/1992 | Lucero et al. | |
| 5,956,971 | A | * | 9/1999 | Cole | F25J 1/0202 62/623 |
| 6,053,007 | A | * | 4/2000 | Victory | F25J 3/0209 62/619 |

(Continued)

OTHER PUBLICATIONS

PCT Search Report and Written Opinion issued in connection with corresponding PCT Application No. PCT/US16/42684 dated Sep. 28, 2016.

(Continued)

*Primary Examiner* — Brian King
(74) *Attorney, Agent, or Firm* — GE Global Patent Operation

(57) ABSTRACT

A process that is configured for treating natural gas mixed with carbon dioxide ($CO_2$) in high concentrations of 30% mole by volume or more. In one embodiment, the process comprises contacting a first feedstream comprising liquid natural gas (LNG) with a feedstock comprising methane to form an overhead product comprising methane vapor and a bottom product comprising carbon dioxide ($CO_2$). The embodiment can also comprise liquefying the methane vapor to form a LNG product and using the LNG product as the liquid natural gas (LNG) in the first feedstream.

16 Claims, 3 Drawing Sheets

(56) References Cited

U.S. PATENT DOCUMENTS

| | | |
|---|---|---|
| 8,282,707 B2 | 10/2012 | Bresler et al. |
| 8,337,593 B2 | 12/2012 | Bresler et al. |
| 2003/0230195 A1 | 12/2003 | Leask |
| 2012/0031144 A1* | 2/2012 | Northrop .................. C10L 3/10 62/617 |
| 2012/0302807 A1 | 11/2012 | Elseviers |
| 2013/0152628 A1* | 6/2013 | Find ........................ B01D 1/28 62/620 |

OTHER PUBLICATIONS

Berstad et al., Low-temperature CO2 removal from natural gas, Energy Procedia, pp. 41-48, vol. 26 (2012), Elseveir Ltd.
W.S. Fyfe et al., Is CO2 Disposal Possible? Am. Chem. Soc. Division of Fuel Chemistry 41:4, 1433-35 (1996); available online at http://web.anl.gov/PCS/acsfuel/preprint%20archive/Files/41_4_ORLANDO_08-96_1433.pdf.
Brian Hitchon et al., The Serendipitous Association of Sedimentary Basins and Greenhouse Gases, Am. Chem. Soc. Division of Fuel Chemistry 41:4, 1428-1432 (1996); available online at https://web.ani.gov/PCS/acsfuel/preprint%20archive/Files/41_4_OR-LANDO_08-96_1428.pdf.
H. Teng et al., The Effect of Hydrate Formation on CO2 Jet instability, Am. Chem. Soc. Division of Fuel Chemistry 41:4, 1447-1457 (1996); available online at https://web.anl.gov/PCS/acsfuel/preprint%20archive/Files/41_4 ORLANDO_08-96_1447.pdf.
Takayuki Saito et al., Highly Efficient Disposal of CO2 into the Ocean by Gas-Lift Method (Basic Characteristics of Glad System), Am. Chem. Soc. Division of Fuel Chemistry 41:4, 1441-1446 (1996); available online at https://web.anl.gov/PCS/acsfuel/preprint%20archive/Files/41_4_ORLANDO_08-96_1441.pdf.
Orlando Leal et al., Carbon Dioxide Removal from Natural Gas using Amine Surface Bonded Adsorbents, Am. Chem. Soc. Division of Fuel Chemistry 41:4, 1332-1340 (1996); available online at https://web.anl.gov/PCS/acsfuel/preprint%20archive/Files/41_4_ORLANDO_08-96_1332.pdf.
Ag.Kh Mamedov, CO2 Reduction Reactions in Heterogeneous Oxidation and Catalytic Cracking Processes, Am. Chem. Soc. Division of Fuel Chemistry 41:4, 1425-1427 (1996); available online at https://web.anl.gov/PCS/acsfuel/preprint%20archive/Files/41_4_ORLAND0_08-98_1425.pdf.
Jan Augustynski et al., Electroreduction of Carbon Dioxide in Aqueous Solutions at Metal Electrodes, Am. Chem. Soc. Division of Fuel Chemistry 41:4, 1420-1424 (1996); available online at https://web.anl.gov/PCS/acsfuel/preprint%20archive/Files/41_4_ORLANDO_08-96_1420.pdf.
Masahiro Fujiwara et al., Hydrogenation of Carbon Dioxide Over Fe—ZnO/HY Composite Catalyst, Am. Chem. Soc. Division of Fuel Chemistry 41:4, 1415-1419 (1996); available online at https://web.anl.gov/PCS/acsfuel/preprint%20archive/Files/41_4_OR-LANDO_08-96_1415.pdf.
Ki-Won Jun et al., Catalytic Hydrogenation of CO2 into Hydrocarbons: Support Effects on Fe and Fe—K Catalysts, Am. Chem. Soc. Division of Fuel Chemistry 41:4, 1411-1414 (1996); available online at https://web.anl.gov/PCS/acsfuel/preprint%20archive/Files/41_4_ORLANDO_08-96_1411. pdf.
Masahiro Saito et al., Methanol Synthesis from CO2 and H2 over Cu/ZnO-based Multicomponent Catalysts, Am. Chem. Soc. Division of Fuel Chemistry 41:4, 1407-1410 (1996): available online at https://web.anl.gov/PCS/acsfuel/preprint%20archive/Files/41_4_ORLANDO_08-96_1407.pdf.
Thomas M. Wahlund et al., Bioconversion of CO2 to Ethanol and Other Compounds, Am. Chem. Soc. Division of Fuel Chemistry 41:4, 1403-1406 (1996); available online at https://web.anl.gov/PCS/acsfuel/preprint%20archive/Files/41_4_ORLANDO_08-96_1403.pdf.
J.S. Lee et al., Current Aspects of Carbon Dioxide Fixation by Microalgae in Korea, Am. Chem. Soc. Division of Fuel Chemistry 41:4, 1397-1402 (1996); available online at https://web.anl.gov/PCS/acsfuel/preprint%20archive/Files/41_4_ORLANDO_08-96_1397.pdf.
John T. Hauck et al., Effects of Simulated Flue Gas on Growth of Microalgae, Am. Chem. Soc. Division of Fuel Chemistry 41:4, 1391-1396 (1996); available online at https://web.anl.gov/PCS/acsfuel/preprint%20archive/Files/41_4_ORLANDO_08-96_1391.pdf.
Sang-Eon Park et al., Activation of Carbon Dioxide as an Oxidant over ZSM-5 Zeolite-Supported Metal Oxide Catalysts, Am. Chem. Soc. Division of Fuel Chemistry 41:4, 1387-1390 (1996); available online at https://web.anl.gov/PCS/acsfuel/preprint%20archive/Files/41_4_ORLANDO_08-96_1387.pdf.
Kamel H. Fotouh et al., CO2 Utilization by Gas Discharges, Am. Chem. Soc. Division of Fuel Chemistry 41:4, 1382-1386 (1996); available online at https://web.anl.gov/PCS/acsfuel/preprint%20archive/Files/41_4_ORLANDO_08-96_1382.pdf.
Kiyohisa Ohta et al., Photoelectrochemical Reduction of CO2 using Silicate Rock Powder Suspended in Water, Am. Chem. Soc. Division of Fuel Chemistry 41:4, 1378-1381 (1996); available online at https://web.anl.gov/PCS/acsfuel/preprint%20archive/Files/41_4_ORLANDO_08-96_1378.pdf
Yoshiyuki Sasaki, Acetylene-mediated Alkylation of Monoalkyl Carbonates and Carbamic Acids with Tert-Amine, Am. Chem. Soc. Division of Fuel Chemistry 41:4, 1368-1377 (1996); available online at https://web.anl.gov/PCS/acsfuel/preprint%20archive/Files/41_4_ORLANDO_08-96_1368.pdf.
August R. Brun-Tcekhovoi et al., The Stable High Temperature CO2-Acceptor Thermoanalytical Study, Am. Chem. Soc. Division of Fuel Chemistry 41:4, 1360-1367 (1996); available online at https://web.anl.gov/PCS/acsfuel/preprint%20archive/Files/41_4_ORLANDO_08-96_1360.pdf.
Shuping Bi, Acid Rain Promoting the Accumulation of CO2 in Surface Waters?!, Am. Chem. Soc. Division of Fuel Chemistry 41:4, 1355-1359 (1996); available online at https://web.anl.gov/PCS/acsfuel/preprint%20archive/Files/41_4_ORLANDO_08-96_1355.pdf.
Masaya Kuno, New Era Will Come with New Concept in Refinery, Am. Chem. Soc. Division of Fuel Chemistry 41:4, 1350-1354 (1996); available online at https://web.anl.gov/PCS/acsfuel/preprint%20archive/Files/41_4_ORLANDO_08-96_1350.pdf.
Yuanji Dong et al., Biomass Reactivity in Gasification by the Hynol Process, Am. Chem. Soc. Division of Fuel Chemistry 41:4, 1345-1349 (1996); available online at https://web.anl.gov/PCS/acsfuel/preprint%20archive/Files/41_4_ORLANDO_08-96_1345.pdf.
Michele Aresta et al., Carbon Dioxide Utilisation in the Chemical Industry, Am. Chem. Soc. Division of Fuel Chemistry 41:4, 1341-1344 (1996); available online at https://web.anl.gov/PCS/acsfuel/preprint%20archive/Files/41_4_ORLANDO_08-96_1341.pdf.
Arturo A. Keller et al., Modellng the Oceanic Storage of Fossil Fuel Emissions, Am. Chem. Soc. Division of Fuel Chemistry 41:4, 1436-1440 (1996); available online at https://web.anl.gov/PCS/acsfuel/preprint%20archive/Files/41_4_ORLANDO_08-96_1436.pdf.

* cited by examiner

USING METHANE REJECTION TO PROCESS A NATURAL GAS STREAM

BACKGROUND

Processing systems may be required to separate a multi-component feedstock into one or more product streams. One of these product streams may be rich in a target component found in the feedstock. For hydrocarbon processing, the target component may be a gas or liquid that retains value on the market as a fuel. Methane (or natural gas) is a fuel gas with many uses for heating, cooking, generating electricity, and powering vehicles, among myriad applications. However, this fuel gas may be mixed with impurities or contaminants in amounts or percentages that may depend on the location of production and/or recovery.

SUMMARY

The subject matter of this disclosure relates generally to embodiments of an apparatus that can purify multi-component feedstocks. The embodiments are useful to generate methane vapor that meets specifications for production of liquid natural gas (LNG) product. In one implementation, the embodiments are configured to use some of the LNG product in a process to condition a feedstock to generate the high-quality methane vapor. This process can be used at locations where the feedstock has a high concentration of carbon dioxide ($CO_2$), for example, in an amount of approximately 30% per mole by volume or more (as compared to approximately 3% per mole by volume more commonly found in locations where the feedstock exhibits "normal" concentrations of $CO_2$ for production).

This high concentration of $CO_2$ in the feedstock may outstrip the capabilities or, more likely, the economics of other processes and systems. Amine systems (and like solvent-based systems) that could address the high concentration of $CO_2$ would be too large to be economically viable. On the other hand, the embodiments herein can be configured at comparatively lower costs. Capital expenses are lower because the embodiments require fewer components than amine systems. This simplified structure can also lower operating expenses because the embodiments require less electrical power relative to other systems (e.g., amine systems) for use with feedstock that has high concentrations of $CO_2$. Operating expenses are also reduced because the embodiments effectively cycle the LNG product back into the conditioning process. This feature avoids use of consumables (e.g., amine, start-up charge, activated carbon material, amine makeup) that are necessary in amine systems to effectively condition the feedstock. Moreover, by eliminating these consumables, the embodiments may prove safer and less hazardous because there is no need to handle (or dispose of) the toxic and/or corrosive amine solutions and like by-products.

BRIEF DESCRIPTION OF THE DRAWINGS

Reference is now made briefly to the accompanying drawings, in which.

Figure 1:
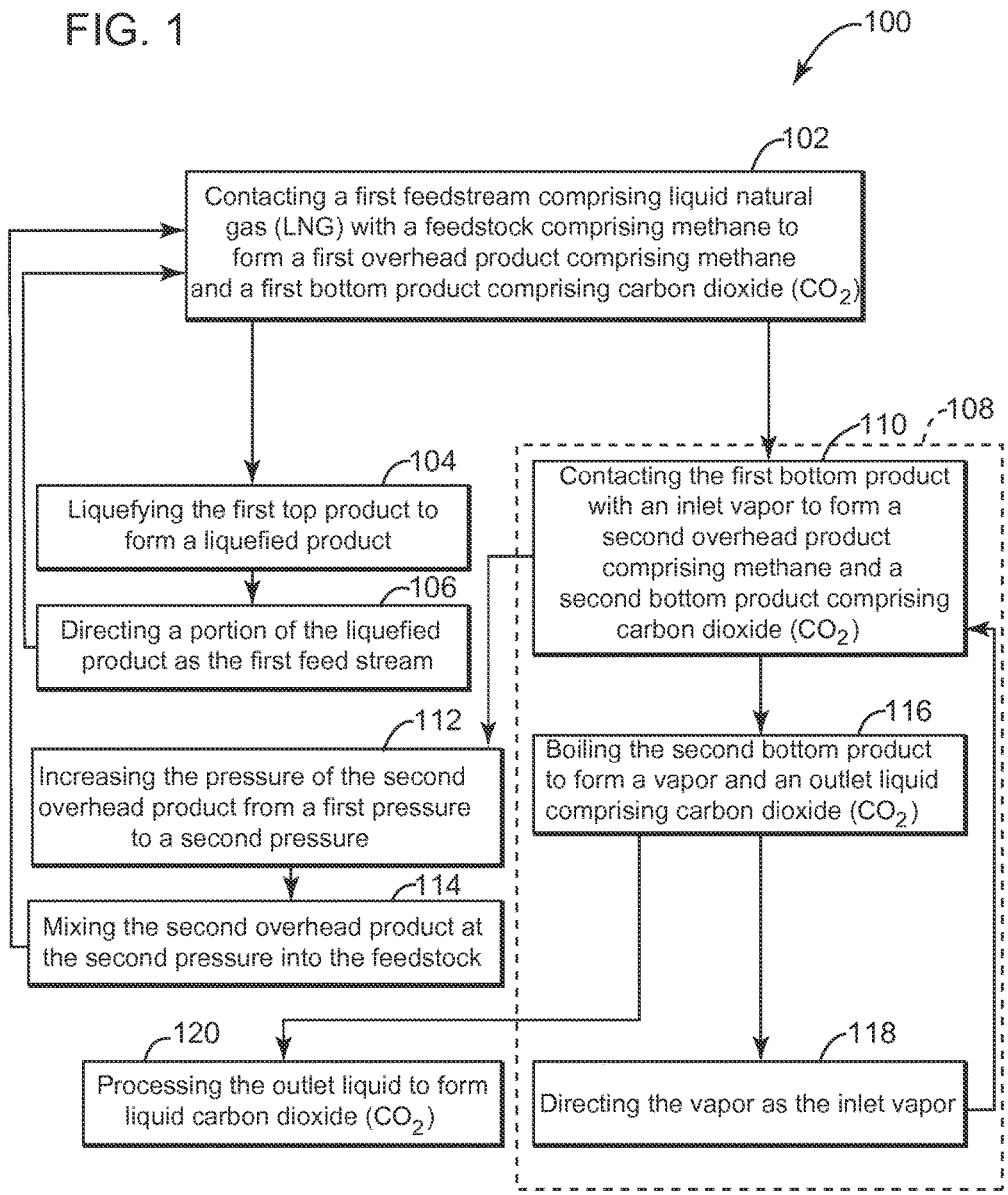
FIG. 1 depicts a flow diagram of an exemplary embodiment of a process to purify a natural gas stream having a high concentration of carbon dioxide ($CO_2$)

Where applicable like reference characters designate identical or corresponding components and units throughout the several views, which are not to scale unless otherwise indicated. The embodiments disclosed herein may include elements that appear in one or more of the several views or in combinations of the several views. Moreover, methods are exemplary only and may be modified by, for example, reordering, adding, removing, and/or altering the individual stages.

DETAILED DESCRIPTION

The discussion below describes various embodiments of processes to extract methane, or natural gas, from a feedstock having a high concentration of carbon dioxide ($CO_2$). These embodiments result in methane vapor that meets specifications for liquefaction to liquid natural gas (LNG). As noted more below, the embodiments are configured to cycle some of the liquid natural gas (LNG) in contact with the methane-rich feedstock. This feature reduces the size and costs of the processing apparatus, while at the same time producing high-quality methane vapor and, in one example, a stream of liquefied carbon dioxide ($CO_2$) that can be used for enhanced recovery of oil and/or further refined for use as a product in industrial or food grade production processes. Other embodiments are within the scope of the disclosed subject matter.

FIG. 1 illustrates a flow diagram of an exemplary embodiment of a process 100 to obtain natural gas from a feedstock. This embodiment may include, at stage 102, contacting a first feedstream comprising liquid natural gas (LNG) with a feedstock comprising methane to form a first overhead product comprising methane and a first bottom product comprising carbon dioxide ($CO_2$). The process 100 can also include, at stage 104, liquefying the first overhead product to form a liquefied product and, at stage 106, directing a portion of the liquefied product as the first feedstream (for use in stage 102). The process 100 can also include, at stage 108, distilling the first bottom product. In the process 100, stage 108 may include, at stage 110, contacting the first bottom product with an inlet vapor to form a second overhead product comprising methane and a second bottom product comprising carbon dioxide ($CO_2$). The process 100 may further include, at stage 112, increasing the pressure of the second overhead product from a first pressure to a second pressure and, at stage 114, mixing the second overhead product at the second pressure into the feedstock. In the process 100, stage 108 may also include, at stage 116, boiling the second bottom product to form a vapor and an outlet liquid comprising carbon dioxide ($CO_2$). The process 100 can further include, at stage 118, directing the vapor as the inlet vapor (for use at stage 110) and, at stage 120, processing the outlet liquid to form liquid carbon dioxide ($LCO_2$).

Figure 2:
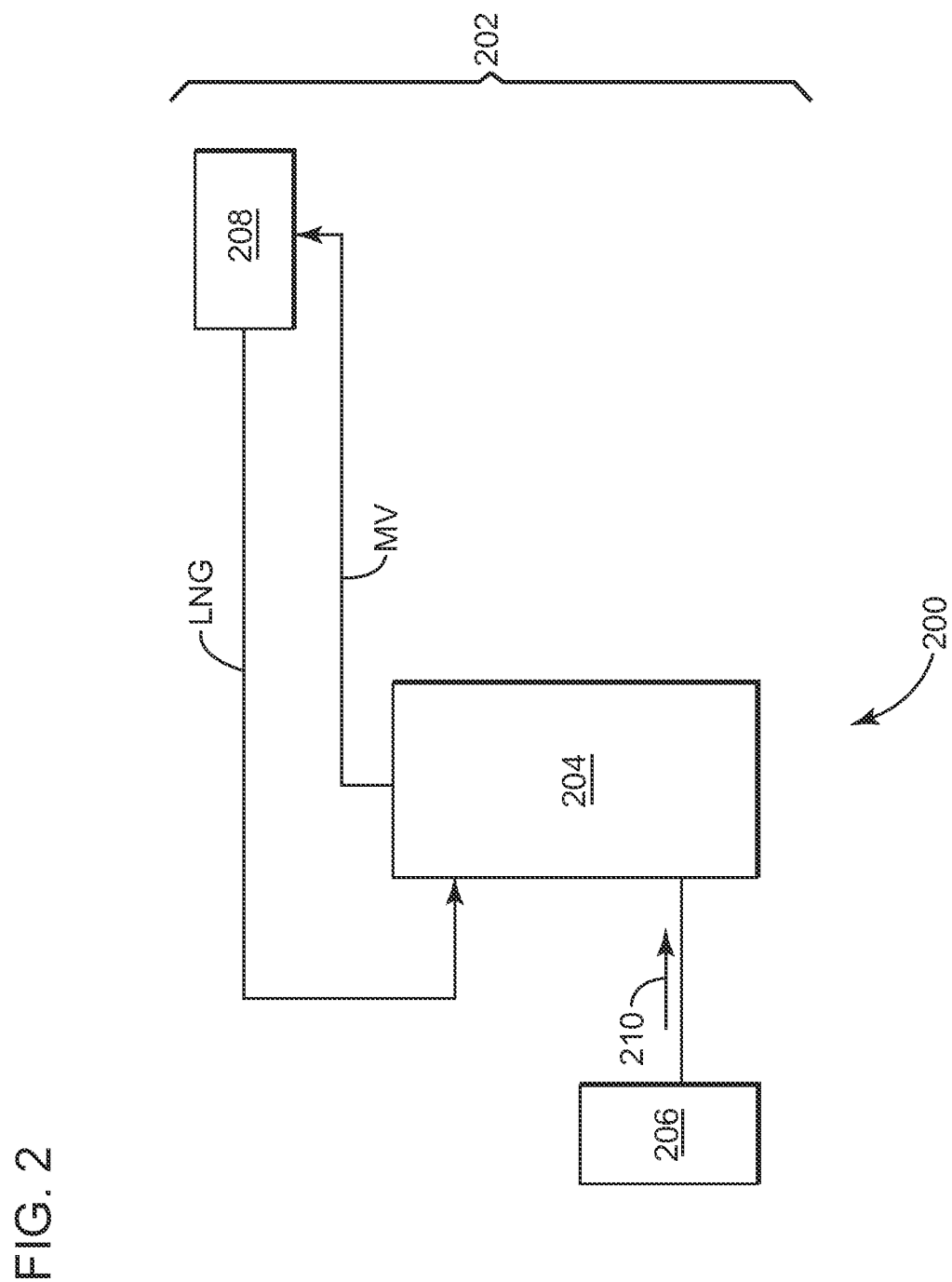
FIG. 2 depicts a schematic diagram of an exemplary embodiment of an apparatus that is configured to implement one or more stages of the process of FIG. 1.
Figure 3:
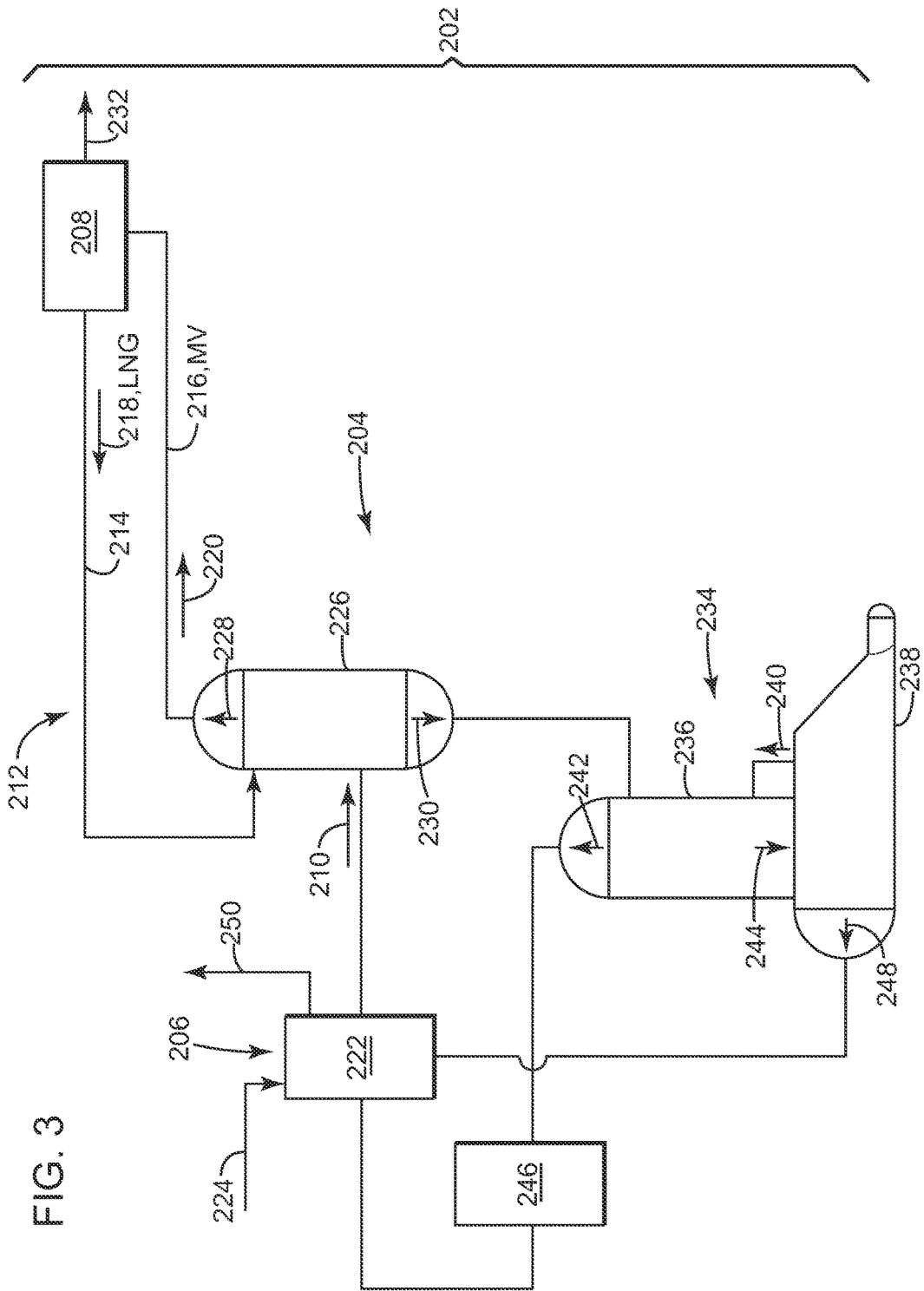
FIG. 3 depicts a schematic diagram of an example of a processing system that includes the apparatus of FIG. 2 to implement one or more stages of the process of FIG. 1.

FIGS. 2 and 3 illustrate, schematically, an exemplary embodiment of hardware in a first configuration to implement one or more stages of the process 100 shown in FIG. 1. As noted above, the process 100 is useful at least because it can reduce the size and costs of the hardware necessary to capture natural gas from feedstock having, in particular, a high concentration of carbon dioxide ($CO_2$). In FIG. 2, the configuration focuses on an example of an apparatus for contacting the feedstock comprising methane with liquid natural gas (LNG). The apparatus can be part of a processing system that can facilitate one or more other stages of the process 100 of FIG. 1. FIG. 3 depicts an example of the apparatus and the processing system. This disclosure contemplates that the configuration of FIGS. 2 and 3 is exemplary only in that various hardware and configurations may exist to execute one of more of the stages of the process 100 to process the feedstock as discussed herein.

FIG. 2 illustrates a schematic diagram of an exemplary embodiment of an apparatus 200 that is configured to purify a natural gas feedstock. The apparatus 200 is part of a processing system, identified generally by the numeral 202. At a high level, the apparatus 200 may include a rejection unit 204 that couples within the system 202 to one or more sources (e.g., a first source 206 and a second source 208). The first source 206 can provide a natural gas feedstock 210 to the rejection unit 204. Examples of the natural gas feedstock 210 can comprise methane in combination with carbon dioxide ($CO_2$) and other components, as applicable. For purposes of the present example, the second source 208 may comprise a liquefaction unit (also, "liquefaction unit 208") that can provide liquid natural gas (LNG) to the rejection unit 204. The liquid natural gas (LNG) is considered "pure" or "purified" and, thus, introduces few contaminates into the rejection unit 204. The "pure" liquid natural gas (LNG) may be useful to drive processes (e.g., methane rejection) in the rejection unit 204. These processes can generate methane vapor (MV) from the "impure" natural gas feedstock 210.

The system 202 can direct the methane vapor (MV) from the rejection unit 204 to the liquefaction unit 208. For purposes of the present example, the liquefaction unit 208 can liquefy the methane vapor (MV) to the "pure" liquid natural gas (LNG). In this way, the system 202 is configured to form a closed loop between the rejection unit 204 and the liquefaction unit 208. This configuration effectively foregoes the need for consumables to facilitate methane rejection in the rejection unit 204 in lieu of the liquid natural gas (LNG) product from the liquefaction unit 208. Moreover, using the "pure" liquid natural gas (LNG) allows the rejection unit 204 to condition the "impure" natural gas feedstock 210 at temperatures low enough so as to effectively pre-cool the methane vapor (MV) at higher pressures prior to liquefaction (in the liquefaction unit 208), but not low enough to solidify (or freeze-out) $CO_2$ into solids that could clog and/or disrupt operation of the rejection unit 204.

FIG. 3 illustrates a schematic diagram of an example of the apparatus 200 and the processing system 202. The system 202 may include a feed loop 212 that couples the liquefaction unit 208 with the rejection unit 204. The feed loop 212 may have a pair of paths (e.g., a first path 214 and a second path 216). The paths 214, 216 can comprise conduits and/or piping to carry fluids (e.g., gasses and liquids). These conduits allow the units 206, 208 to exchange a pair of feedstreams (e.g., a first feedstream 218 and a second feedstream 220). The first feedstream 218 can comprise the "pure" liquid natural gas (LNG). The second feedstream 220 can comprise methane vapor (MV) that is the result of processes that occur at the rejection unit 204.

The first source 206 may include a pretreatment unit 222 that can be configured to remove impurities from an incoming plant gas feed 224. For hydrocarbons, the incoming plant gas feed 224 may flow through a pipeline directly from a well-head, holding tank, or other repository. The pretreatment unit 222 can remove water and other impurities from the incoming plant gas feed 224. Such processing can result in the natural gas feedstock 210 that the system 202 delivers to the rejection unit 204.

Bulk removal of $CO_2$ from the natural gas feedstock 210 occurs in the rejection unit 204. In one embodiment, the rejection unit 204 may include a contactor column 226 that receives the natural gas feedstock 210 from the pretreatment unit 222 and the first feedstream 218 from the liquefaction unit 208. Examples of the contactor column 226 can leverage any one of several constructions for gas-liquid contactors. Such constructions can contact the natural gas feedstock 210 (e.g., gas) with the first feedstream 218 (e.g., "liquid"). These constructions may include devices (e.g., sieve plates, bubble-cap plates, valve plates, etc.) to enhance the methane rejection processes, as desired.

The natural gas feedstock 210 and the first feedstream 218 can enter the contactor column 226 with properties that are beneficial to generate the methane vapor (MV) of the second feedstream 220. Examples of these properties include temperature, pressure, and flow rate, among others. Values for the properties may be configured to cause the natural gas feedstock 210 to boil (or "vaporize") the first feedstream 218 in the contactor column 226. In use, the processing system 202 may be configured to change the values for one or more of these properties to accommodate for the composition of the natural gas feedstock 210 and/or the first feedstream 218. The values may depend, for example, on the concentration of $CO_2$ (and/or other contaminants) in the natural gas feedstock 210. In other implementations, the values may depend on ambient conditions proximate the apparatus 200 and/or at the location of the processing system 202. These ambient conditions may include temperature, relative humidity, barometric pressure, and the like. Examples of the apparatus 200 may be configured so that the natural gas feedstock 210 and the first feedstream 218 enter the contactor column 226 with properties in an operating range that defines values (approximately) in accordance with Tables 1 and 2 below:

TABLE 1

Exemplary operating range for properties of natural gas feedstock 210

| Property | Approx. Minimum | Approx. Maximum |
| --- | --- | --- |
| Temperature (° F.) | −33 | −27 |
| Pressure (kPA) | 4000 | 4300 |
| Flow rate (ft/min) | 130 | 175 |

TABLE 2

Exemplary operating range for properties of first feedstream 218

| Property | Approx. Minimum | Approx. Maximum |
| --- | --- | --- |
| Temperature (° F.) | −133 | −129 |
| Pressure (kPA) | 4000 | 4300 |
| Flow rate (actual ft³/min) | 52 | 55 |

The boiling process in the contactor column 226 can result in one or more products (e.g., a first overhead product 228 and a first bottom product 230). The products 228, 230 can exit the contactor column 226 at the "top" and the "bottom," respectively. As noted herein, gas and/or vapor can exit the top of the contactor column 226. Liquid can exit the bottom of the contactor column 226.

At the top of the contactor column 226, the first overhead product 228 can comprise methane vapor that can be considered "purified" because its composition contains a very low percentage of $CO_2$ (e.g., approximately 10 mole part per million by volume). The methane vapor can exit the contactor column 226 at a temperature from approximately −122° F. to approximately −128° F. and a pressure from approximately 4000 kPA to approximately 4300 kPA. The system 202 can direct the methane vapor (as the second feedstream 220) to the liquefaction unit 208, e.g., via the second path 216 of the feed loop 212. As noted above, implementation of the process 100 (FIG. 1) is at least beneficial because the methane vapor is effectively pre-cooled (at higher pressure) prior to liquefaction. The liquefaction unit 208, in turn, can convert the methane vapor to form a first useable product 232, typically a liquefied natural gas (LNG) product (also, "LNG product"). In one implementation, the system 202 can be configured to direct (or re-direct) a portion of the LNG product back to the contactor column 226 as the liquid natural gas (LNG) of the first feedstream 218.

At the bottom of the contactor column 226, the first bottom product 230 can comprise contaminants including $CO_2$. It is not uncommon for the first bottom product 230 to also comprise other components like methane (but as a percentage that is smaller than the percentage of methane in the methane vapor of the first overhead product 228). In one implementation, the first bottom product 230 can form a liquid stream that can exit the contractor column 226 at a temperature from approximately −40° F. to approximately −50° F. and a pressure from approximately 4000 kPA to approximately 4300 kPA. The system 202 may direct this liquid stream to a recovery unit 234 at a flow rate of from approximately 6 actual ft$^3$/min to approximately 7 actual ft$^3$/min.

The recovery unit 234 is useful to recover methane that is residual in the liquid stream that exits the contactor column 226 as the first bottom product 230. In one implementation, the recovery unit 234 can include a distillation apparatus that is useful for distilling the liquid stream of the first bottom product 230 (at stage 108 of FIG. 1). This distillation apparatus may include a fractionating column 236 and a re-boiler 238. This disclosure does contemplate, however, that the system 202 may include and/or utilize other components (e.g., condenser, pumps, reservoir drums, etc.) to appropriately fractionate methane (and/or other components) from the liquid stream that enters the fractionating column 236.

The fractionating column 236 can introduce an inlet vapor 240 to the liquid stream. Properties for the inlet vapor 240 and the liquid stream that enter the fractionating column 236 are configured for the inlet vapor 240 to effectively boil (or "vaporize") the liquid stream. These properties may fall within an operating range that defines values (approximately) in accordance with Tables 3 and 4 below:

TABLE 3

Exemplary operating range for properties
of first bottom product 230

| Property | Approx. Minimum | Approx. Maximum |
| --- | --- | --- |
| Temperature (° F.) | −50 | −40 |
| Pressure (kPA) | 4000 | 4300 |
| Flow rate (actual ft$^3$/min) | 6 | 7 |

TABLE 4

Exemplary operating range for properties of inlet vapor 240

| Property | Approx. Minimum | Approx. Maximum |
| --- | --- | --- |
| Temperature (° F.) | 40 | 50 |
| Pressure (kPA) | 4000 | 4300 |
| Flow rate (ft$^3$/min) | 25 | 30 |

The boiling process in the fractionating column 236 forms one or more products (e.g., a second overhead product 242 and a second bottom product 244). The products 242, 244 can exit the fractionating column 236 at the "top" and the "bottom," respectively. As noted herein, gas and/or vapor can exit the top of the fractionating column 236. Liquid can exit the bottom of the fractionating column 236.

In one implementation, the second overhead product 242 can comprise methane vapor that is residual in the liquid stream (of the first bottom product 230). The methane vapor can exit the fractionating column 236 at a temperature from approximately −40° F. to approximately −50° F. and a pressure from approximately 4000 kPA to approximately 4300 kPA. The system 202 can direct the methane vapor to a recompression unit 246 at a flow rate from approximately 10 actual ft$^3$/min to approximately 13 actual ft$^3$/min. Examples of the recompression unit 246 can be configured with one or more pumps (and/or other collateral equipment) to raise the pressure of the methane vapor from a first pressure that is different from the first pressure. In one implementation, the first pressure is in a range of from approximately 4000 kPA to approximately 4300 kPA) and the second pressure (in a range of from approximately 5200 kPA to approximately 5500 kPA). The system 202 can direct the pressurized methane vapor at the second pressure from the recompression unit 246 to the pretreatment unit 222. The pressurized methane vapor may have a flow rate from approximately 10 actual ft$^3$/min to approximately 13 actual ft$^3$/min. The pretreatment unit 222 can be configured to mix the pressurized methane vapor with and/or otherwise formulate the pressurized methane vapor for use in and/or as at least part of the feedstock 210.

The second bottom product 244 can exit the fractionating column 236 as a liquid stream that is rich in $CO_2$. The liquid stream can enter the re-boiler 238 at a temperature from approximately 40° F. to approximately 50° F. and a pressure from approximately 4000 kPA to approximately 4300 kPA. Operation of the re-boiler 238 may form the inlet vapor 240 from the liquid stream of the second bottom product 244 to drive distillation of the liquid stream of the first bottom product 230 that enters the fractioning column 236, as noted above. In one implementation, the re-boiler 238 may form an outlet stream 248 that comprises carbon dioxide ($CO_2$) in liquid form. The outlet stream 248 can exit the re-boiler 238 at a temperature from approximately 40° F. to approximately 50° F. and a pressure from approximately 4000 kPA to approximately 4300 kPA. The system 202 can be configured to direct the outlet stream 248 to the pretreatment unit 222 at a flow rate from approximately 4 actual ft$^3$/min to approximately 7 actual ft$^3$/min. The pretreatment unit 222 may further process (e.g., boil, liquefy, etc.) the outlet stream 248 to generate a second useable product 250 in the form of liquid $CO_2$ ($LCO_2$).

As used herein, an element or function recited in the singular and proceeded with the word "a" or "an" should be understood as not excluding plural said elements or functions, unless such exclusion is explicitly recited. Furthermore, references to "one embodiment" should not be interpreted as excluding the existence of additional embodiments that also incorporate the recited features.

This written description uses examples to disclose the embodiments, including the best mode, and also to enable any person skilled in the art to practice the embodiments, including making and using any devices or systems and performing any incorporated methods. The patentable scope of the embodiments is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A process for treating natural gas, said process comprising:
    contacting a first feedstream comprising liquid natural gas (LNG) with a feedstock comprising methane and carbon dioxide ($CO_2$), the $CO_2$ present in the feedstock in a concentration of 30% mole by volume or more, to form an overhead product comprising methane and a bottom product comprising carbon dioxide ($CO_2$);
    distilling the bottom product to generate a vapor comprising methane and a liquid comprising carbon dioxide ($CO_2$);
    boiling the liquid to form an inlet vapor for use in distilling the bottom product and an outlet liquid comprising carbon dioxide ($CO_2$); and
    processing the outlet liquid to form liquid carbon dioxide ($CO_2$).

2. The process of claim 1, further comprising liquefying the overhead product to form a liquefied product.

3. The process of claim 2, further comprising directing a portion of the liquefied product as the first feedstream comprising liquid natural gas (LNG).

4. The process of claim 1, wherein the methane in the overhead product has a concentration of 97% mole by volume or more.

5. The process of claim 1, wherein the carbon dioxide ($CO_2$) in the bottom product has a concentration of 80% mole by volume or more.

6. The process of claim 1, further comprising:
    increasing the pressure of the vapor from a first pressure to a second pressure that is different from the first pressure.

7. The process of claim 6, further comprising:
    mixing the vapor at the second pressure into the feedstock.

8. A system for treating natural gas, said system comprising:
    a contactor column;
    a first source coupled with the contactor column, the first source configured to provide a feedstock comprising methane and carbon dioxide ($CO_2$), the $CO_2$ present in the feedstock in a concentration of 30% mole by volume or more; and
    a second source coupled with the contactor column, the second source configured to provide liquid natural gas (LNG), wherein the contactor column is configured to contact the liquid natural gas (LNG) with the feedstock to form a first overhead product comprising methane and a first bottom product comprising carbon dioxide ($CO_2$);
    a fractionating column coupled with the contactor column, wherein the fractionating column is configured for a process that contacts the first bottom product with a vapor to form a second overhead product comprising methane;
    a re-boiler coupled with the fractionating column, wherein the process in the fractionating column forms a second bottom product that comprises carbon dioxide ($CO_2$), and wherein the re-boiler is configured for a process that boils the second bottom product to generate the vapor for contacting with the first bottom product in the fractionating column, and an outlet stream that comprises carbon dioxide ($CO_2$) in liquid form.

9. The system of claim 8, further comprising a feed loop that couples with the contactor column, wherein the feed loop has a first path that is configured to direct the liquid natural gas (LNG) to the contactor column from the second source.

10. The system of claim 9, wherein the second source comprises a liquefaction unit that generates the liquid natural gas (LNG).

11. The system of claim 9, wherein the feed loop has a second path that is configured to direct the first overhead product to the liquefaction unit.

12. A method, comprising:
    contacting liquid natural gas (LNG) with a feedstock comprising methane and carbon dioxide ($CO_2$), the $CO_2$ present in the feedstock in a concentration of 30% mole by volume or more, to form an overhead product and a bottom product;
    liquefying the overhead product to form the liquid natural gas (LNG); and
    processing the bottom product to form liquid carbon dioxide ($CO_2$), wherein the processing the bottom product comprises:
        distilling the bottom product to generate a vapor comprising methane and a liquid comprising carbon dioxide ($CO_2$);
        boiling the liquid to form an inlet vapor for use in distilling the bottom product and an outlet liquid comprising carbon dioxide ($CO_2$);
        processing the outlet liquid to form the liquid carbon dioxide ($CO_2$).

13. The method of claim 12, wherein the overhead product comprises methane in vapor form.

14. The method of claim 1, wherein the bottom product is at a temperature from approximately −40° F. to approximately −50° F. and a pressure from approximately 4000 kPA to approximately 4300 kPA.

15. The method of claim 1, wherein the liquid after distilling is at a temperature from approximately 40° F. to approximately 50° F., and at a pressure from approximately 4000 kPA to approximately 4300 kPA.

16. The method of claim 1, wherein the inlet vapor is at a temperature from approximately 40° F. to approximately 50° F., and at a pressure from approximately 4000 kPA to approximately 4300 kPA.

* * * * *